(12) United States Patent
Kasvikis et al.

(10) Patent No.: US 9,241,715 B2
(45) Date of Patent: Jan. 26, 2016

(54) JAW RESTRAINT

(71) Applicant: COVIDIEN LP, Mansfield, MA (US)

(72) Inventors: Dino Kasvikis, Middletown, CT (US);
Russell Estrella, North Haven, CT (US);
David Farascioni, Bethel, CT (US);
Gregory Pappas, Madison, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/540,439

(22) Filed: Nov. 13, 2014

(65) Prior Publication Data

US 2015/0083738 A1    Mar. 26, 2015

Related U.S. Application Data

(63) Continuation of application No. 12/956,339, filed on Nov. 30, 2010, now abandoned.

(51) Int. Cl.
*A61B 17/068* (2006.01)
*A61B 19/02* (2006.01)
(Continued)

(52) U.S. Cl.
CPC . *A61B 17/07207* (2013.01); *A61B 2017/00362* (2013.01); *A61B 2017/00685* (2013.01); *A61B 2017/07214* (2013.01); *A61B 2017/07221* (2013.01); *A61B 2017/07235* (2013.01); *A61B 2017/07271* (2013.01); *A61B 2019/308* (2013.01)

(58) Field of Classification Search
CPC ............................................... A61B 2017/0688
USPC .................. 24/546, 547, 545, 456, 563, 555;
227/175.2
See application file for complete search history.

(56) References Cited

U.S. PATENT DOCUMENTS 3,231,076 A    1/1966   Freiman
3,485,467 A * 12/1969   Fuchs et al. .................. 24/601.2
(Continued)

FOREIGN PATENT DOCUMENTS

DE           20217850 U1    1/2003
JP          2005-103289 A    4/2005
(Continued)

OTHER PUBLICATIONS

Japanese Office Action dated May 12, 2015 in corresponding JP Application 2011-196362.
(Continued)

*Primary Examiner* — Mickey Yu
*Assistant Examiner* — Allan Stevens (57) ABSTRACT

A jaw restraint is provided to temporarily secure an anvil assembly relative to a cartridge assembly during shipping. The jaw restraint generally includes a body portion having an upper arm for releasably securing the anvil assembly and a lower arm for releasably securing the cartridge assembly. An inwardly projection is provided between the upper and lower arms. The anvil assembly is secured between the upper arm and the inwardly directed projection and the cartridge assembly is secured between the lower arm and the inwardly directed projection. One or more finger members extending proximally from the body portion may be provided to facilitate biasing the upper arm away from the lower arm to release the anvil and cartridge assemblies from the jaw restraint. The jaw restraint may be provided with structure for engagement with shipping packaging.

13 Claims, 12 Drawing Sheets

(51) Int. Cl.
*A61B 17/072* (2006.01)
*A61B 17/00* (2006.01)
*A61B 19/00* (2006.01)

(56) References Cited

U.S. PATENT DOCUMENTS

| | | |
|---|---|---|
| 3,669,491 A | 6/1972 | Weslock |
| 4,450,605 A * | 5/1984 | Schaty ............................ 24/457 |
| 4,765,495 A | 8/1988 | Bisk |
| 5,144,942 A | 9/1992 | Decarie et al. |
| 5,379,895 A | 1/1995 | Foslien |
| 5,392,917 A | 2/1995 | Alpern et al. |
| 5,542,209 A * | 8/1996 | Sheu ................................. 47/44 |
| 6,325,336 B1 * | 12/2001 | Coykendall .................. 248/68.1 |
| 7,134,587 B2 | 11/2006 | Schwemberger et al. |
| 7,147,140 B2 | 12/2006 | Wukusick et al. |
| D648,211 S | 11/2011 | Weaver et al. |
| 2005/0070758 A1 | 3/2005 | Wells et al. |
| 2005/0143759 A1 | 6/2005 | Kelly |
| 2008/0004637 A1 | 1/2008 | Klassen et al. |
| 2010/0072258 A1 | 3/2010 | Farascioni et al. |

FOREIGN PATENT DOCUMENTS

| | | |
|---|---|---|
| JP | 2005-193040 A | 7/2005 |
| JP | 2007-527762 A | 10/2007 |
| JP | 2009-011768 A | 1/2009 |

OTHER PUBLICATIONS

Australian Examination Report dated May 12, 2015 corresponding to AU Application 2011218636.
European Search Report corresponding to EP 11250770.2, completed Feb. 22, 2012; (3 pp.).

* cited by examiner

JAW RESTRAINT

CROSS-REFERENCE TO RELATED APPLICATIONS

The present application is a continuation of U.S. patent application Ser. No. 12/956,339, filed on Nov. 30, 2010. The content of this prior application is incorporated by reference herein in its entirety.

BACKGROUND

1. Technical Field

The present disclosure relates to jaw restraints for use with a jaw assembly of a surgical instrument. More particularly, the present disclosure relates to a removable jaw restraint which temporarily secures first and second jaws of a surgical instrument against movement during shipping.

2. Background of Related Art

Surgical instruments are typically transported from the manufacturer to the end user in sterile shipping packages. Some surgical instruments such as, for example, surgical stapling apparatus contain many movable parts which need to be protected during shipping. Surgical stapling instruments typically include an anvil assembly and an associated cartridge assembly which contains a plurality of staples. The staples are releasably retained within staple pockets formed within the cartridge assembly.

During transportation, the shipping package is often subjected to extensive handling which may result in the shipping package being bumped or shaken. This can result in movement of the staple cartridge assembly within the shipping package and possibly dislodging the staples wholly or partially from within the staple pockets.

Therefore, there exists a need for a jaw restraint which prevents movement of anvil and cartridge assemblies during shipping. Additionally, there exists a need for a jaw restraint which is configured to be easily disengaged from associated anvil and cartridge assemblies. There is still further need for a jaw restraint which can be secured within a shipping package to further secure the anvil assembly and cartridge assembly within the shipping package.

SUMMARY

There is disclosed a jaw restraint for releasably securing a first jaw of a tool assembly relative to a second jaw of the tool assembly to prevent movement of various components of the tool assembly during shipping. The jaw restraint generally includes a first arm for supporting a first jaw of the tool assembly and a second arm for supporting a second jaw of the tool assembly. A projection is directed inwardly between the first and second arms and is provided to be positioned within the first and second jaws of the tool assembly. A first portion connects the first arm to the projection and a second portion connects the second arm to the projection. The first and second portions are arcuate in shape and face in a first direction. The projection is also arcuate in shape and faces in a second direction generally opposite to that of the first direction.

The jaw restraint additionally includes a finger member extending from the first portion to facilitate biasing the first arm away from the second arm. The finger member extends in a direction opposite that of the first arm. The first arm includes a first inwardly directed lip having an enlarged distal end to prevent sideways movement of an associated anvil or cartridge assembly.

In a specific embodiment, the projection is formed from a flexible material. For example, the projection is formed of a polymeric material. In an alternative embodiment, the entire jaw restraint may be formed of a flexible material. In a particular embodiment, a first finger member extends from the first portion of the jaw restraint and a second finger member extends from the second portion of the jaw restraint.

There is also disclosed a jaw restraint for securing a first jaw of a tool assembly relative to a second jaw of the tool assembly. The jaw restraint includes a body portion having a first arm for supporting a first jaw of a tool assembly and a second arm for supporting a second jaw of the tool assembly. A projection is directed inwardly between the first and second arms. A first portion connects the first arm to the projection and a second portion connects the second arm to the projection. A finger member extends from the body portion. In a more specific embodiment, two finger members extend independently from the body portion. The two finger members are provided to be biased together in order to move the upper and lower arms away from each other.

There is still further disclosed a jaw restraint for use with a suture package. The jaw restraint includes a body portion having a first arm for supporting a first jaw of a tool assembly and a second arm for supporting a second jaw of the tool assembly. A projection is directed inwardly between the first and second arms and first and second portions connect the first and second arms, respectively, to the projection. A finger member extends proximally from the body portion and includes a cut out for engagement with a suture package. In one embodiment, the cut out is formed in a proximal edge of the finger member. In another embodiment, the cut out is formed in a side edge of the finger member. In still another embodiment, the cut out is formed through a generally central area of the finger member.

There is also disclosed a shipping package assembly having a shipping package and a jaw restraint including a body portion. The body portion includes a first arm for supporting a first jaw of a tool assembly and a second arm for supporting a second jaw of the tool assembly. A projection is directed inwardly between the first and second arms and is connected to the first and second arms by respective first and second portions. A finger member extends proximally from the body portion and includes a cut out. The suture package has a projection for engagement with the cut out in the finger member in order to secure the jaw restraint to the suture package.

DESCRIPTION OF THE DRAWINGS

Various embodiments of the presently disclosed jaw restraint are disclosed herein with reference to the drawings, wherein.

DETAILED DESCRIPTION OF EMBODIMENTS

Embodiments of the presently disclosed jaw restraint will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
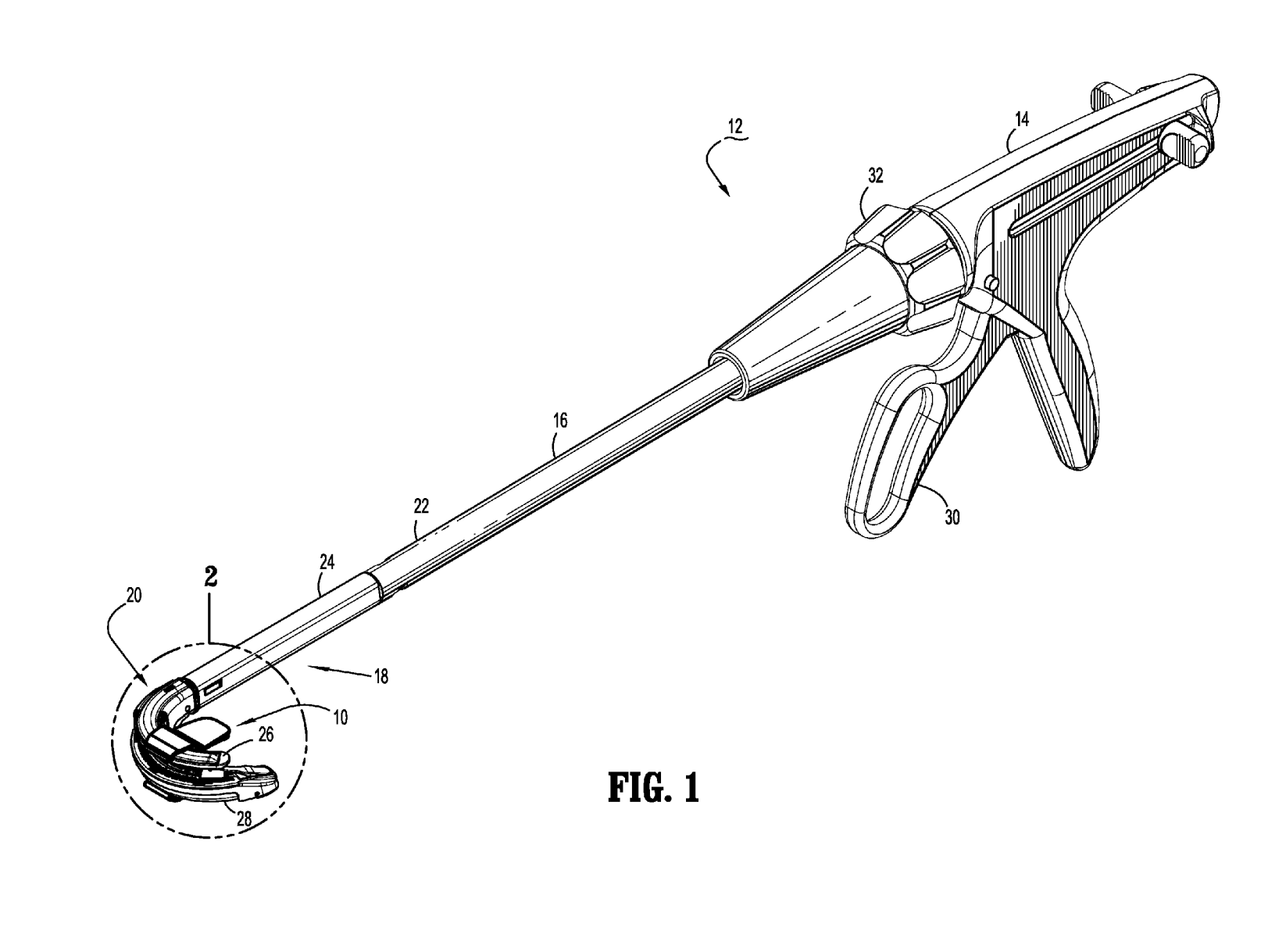
FIG. 1 is a perspective view of one embodiment of a jaw restraint positioned about a tool or jaw assembly of a surgical instrument.

Referring initially to FIG. 1 there is disclosed one embodiment of a jaw restraint 10 for use with a surgical stapling instrument 12. Surgical stapling instrument 12 generally includes a handle assembly 14 having an elongate member 16 extending distally from handle assembly 14. A loading unit 18, including a tool or jaw assembly 20, is removably attached to a distal end 22 of elongate member 16. Jaw assembly 20 generally includes an anvil member 26 and the cartridge assembly 28. A jaw assembly 20 is movable from an open position to a closed position in which anvil assembly 26 and cartridge assembly 28 are in close cooperative alignment. A trigger 30 is provided on handle assembly 14 to move anvil assembly 26 from the open position to the closed position relative to cartridge assembly 28. A rotation knob 32 is provided on elongate member 16 in order to rotate jaw assembly 20 with respect to the handle assembly 14 and relative to the tissues being operated upon.

Jaw restraint 10 is provided to maintain anvil assembly 26 in the open position relative to cartridge assembly 28 during shipping of loading unit 18, in a manner described in more detail hereinbelow. By maintaining anvil assembly 26 and the open position relative to cartridge assembly 28, jaw restraint 10 prevents shifting of, or damage to, internal components associated with anvil assembly 26 or cartridge assembly 28 due to bumping, crushing, etc. during shipment.

While jaw restraint 10 is described for use with surgical stapling instrument 12, it is contemplated that jaw restraint 10 is useful with other surgical instruments having a pair of jaw members such as, for example, surgical stapling instruments including parallel jaw members, electro-surgical instruments used to join tissue, etc.

Figure 2:
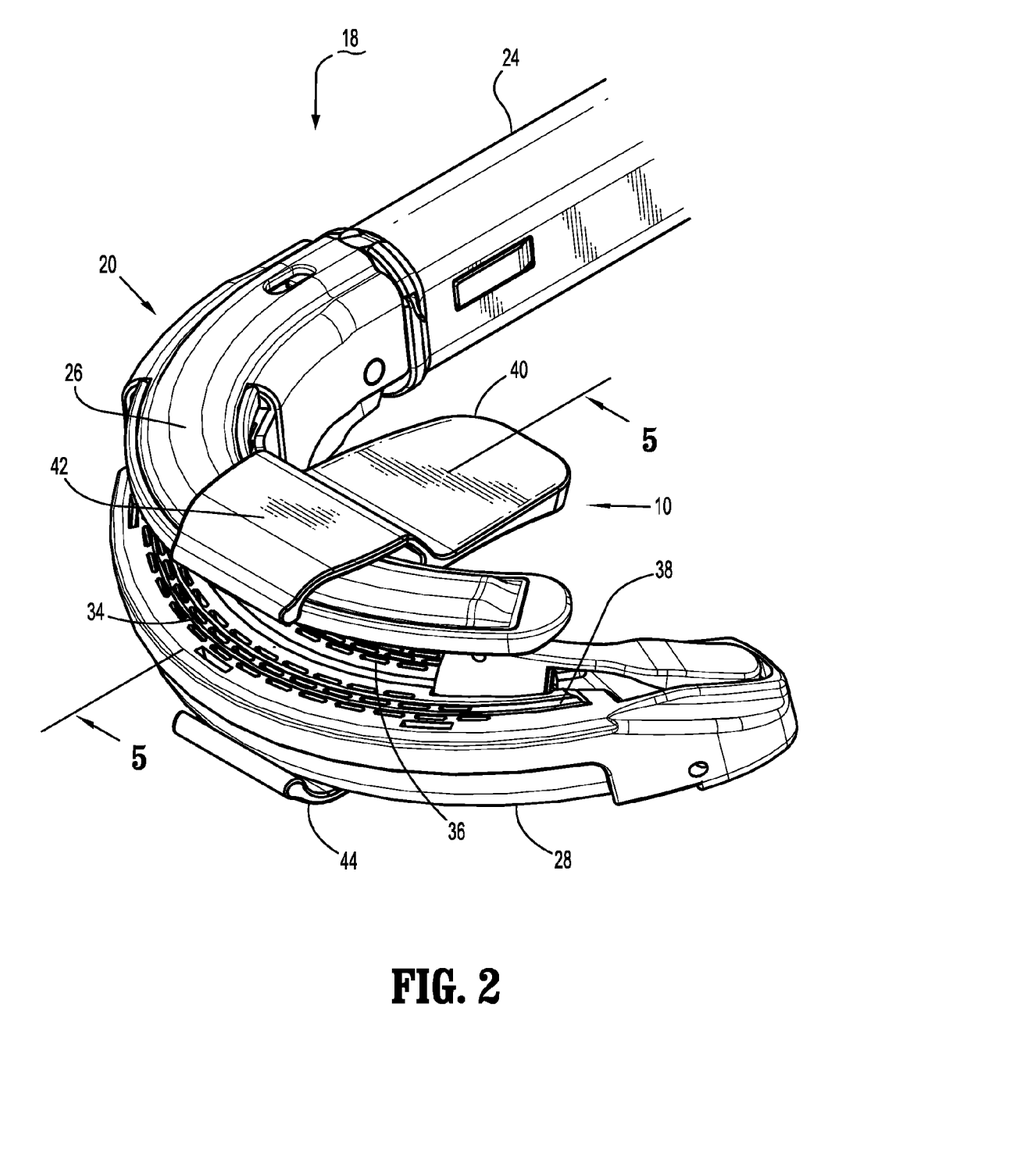
FIG. 2 is an enlarged perspective view of the jaw restraint of FIG. 1 positioned about the jaw assembly.

Referring now to FIG. 2, there is disclosed an enlarged view of loading unit 18 including tool assembly 20 and jaw restraint 10. As shown, cartridge assembly 28 includes first and second longitudinally extending rows of staple containing pockets 34 and 36. A knife slot 38 extends longitudinally through cartridge assembly 28 between first and second rows of staple containing pockets 34 and 36. In this embodiment, the cartridge assembly 28 has three rows of staples on either side of the knife. It is contemplated herein that the disclosed jaw restraint can be used with cartridge assemblies having less than three rows of staples on either side of the knife. While not specifically shown, jaw restraint 10 is provided to maintain and stabilize anvil assembly 26 and cartridge assembly 28 in order to prevent staples (not shown) from being bumped or ejected out of the rows of staple containing pockets 34 and 36.

As shown, jaw restraint 10 includes a finger member 40 to facilitate manipulation of jaw restraint 10 about anvil assembly 26 and cartridge assembly 28. Jaw restraint 10 includes a first or upper arm 42 which is provided to engage and stabilize anvil assembly 26 and a second or lower arm 44 which is provided to engage and stabilize cartridge assembly 28. The first arm 42 is arcuate in shape and forms a first recess "recess 42a" for receiving the jaw of the tool assembly. The second arm 44 can have a similar shape and forms a second recess "recess 44a" for receiving the jaw of the tool assembly, where the restraint engages a surgical stapling tool, the arm for engaging the cartridge assembly has a greater depth "d" than the other arm.

Figure 3:
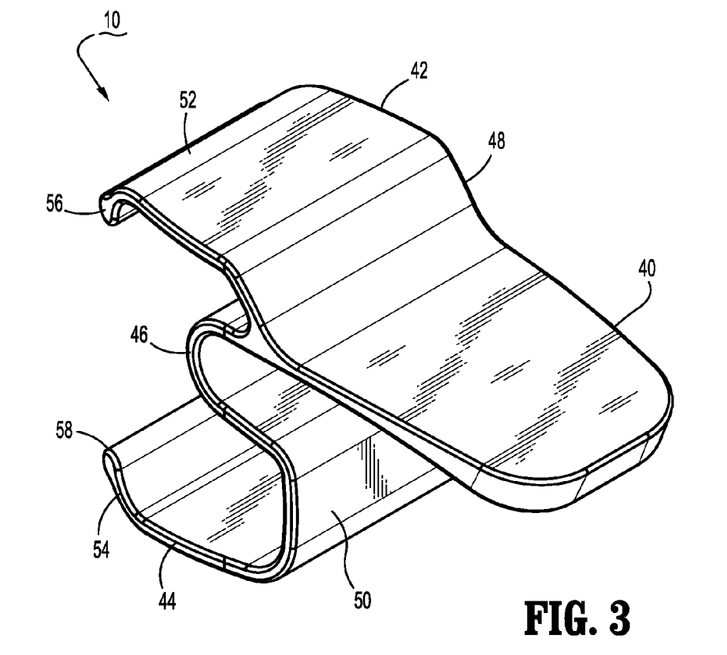
FIG. 3 is a perspective view of the jaw restraint of FIG. 1.
Figure 4:
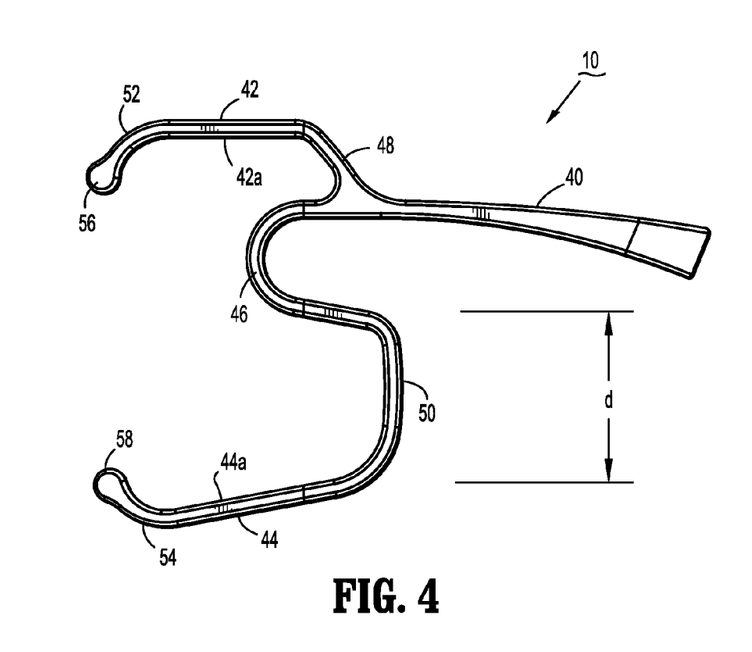
FIG. 4 is a side view of the jaw restraint of FIG. 1.

Referring now to FIGS. 3 and 4, jaw restraint 10 is at least partially formed of a generally flexible material in order to be easily removed from about anvil assembly 26 and cartridge assembly 28. Jaw restraint 10 may be formed from a variety of materials such as polymeric copolymer materials, stainless steel, shape memory alloys, etc. Additionally, while jaw restraint 10 is illustrated as formed from generally thin rectangular material, it is also contemplated that jaw restraint 10 maybe formed from materials having other cross-sections such as, for example, tubular, solid circular, etc.

A resilient portion extends between the arms 42, 44. Thus, jaw restraint 10 includes a resilient inwardly facing projection 46 in this embodiment provided between upper and lower arms 42 and 44. Inwardly facing projection 46 is flexible relative to upper and lower arms 42 and 44. Inwardly facing projection 46 functions as a hinge and is provided to bias upper and lower arms 42 and 44 into a first or closed position. Additionally, inwardly facing projection 46 is provided to extend between anvil assembly 26 and cartridge assembly 28 in order to prevent any relative movement there between during shipment. In the disclosed embodiment only one inwardly facing projection is shown, however, it is contemplated that more than one inwardly projection can be used. Upper arm 42 is connected to inwardly facing projection 46 by a first arcuate member or portion 48. Likewise, lower arm 44 is connected to inwardly facing projection 46 by a second arcuate member or portion 50. Inwardly facing projection 46 also has a generally arcuate shape facing generally in an opposite direction from first and second arcuate portions 48 and 50.

In this embodiment, finger member 40 extends proximally from first arcuate portion 48. In order to inhibit anvil assembly 26 and cartridge assembly 28 from sliding sideways out between upper arm 42 and lower arm 44, upper and lower arms 42 and 44 are provided with first and second inwardly directed lips 52 and 54. First and second inwardly directed lips 52 and 54 are provided with respective enlarged distal ends 56 and 58 to further inhibit any sideways movement of anvil assembly 26 and cartridge assembly 28 relative to jaw restraint 10.

It should be noted that, the various disclosed jaw restraints and elements of the jaw restraint, such as jaw restraint 10, may be formed as a single, integral body member or, alternatively may be formed from separate components joined together through various known methods such as, for example, welding, gluing, etc.

Figure 5:
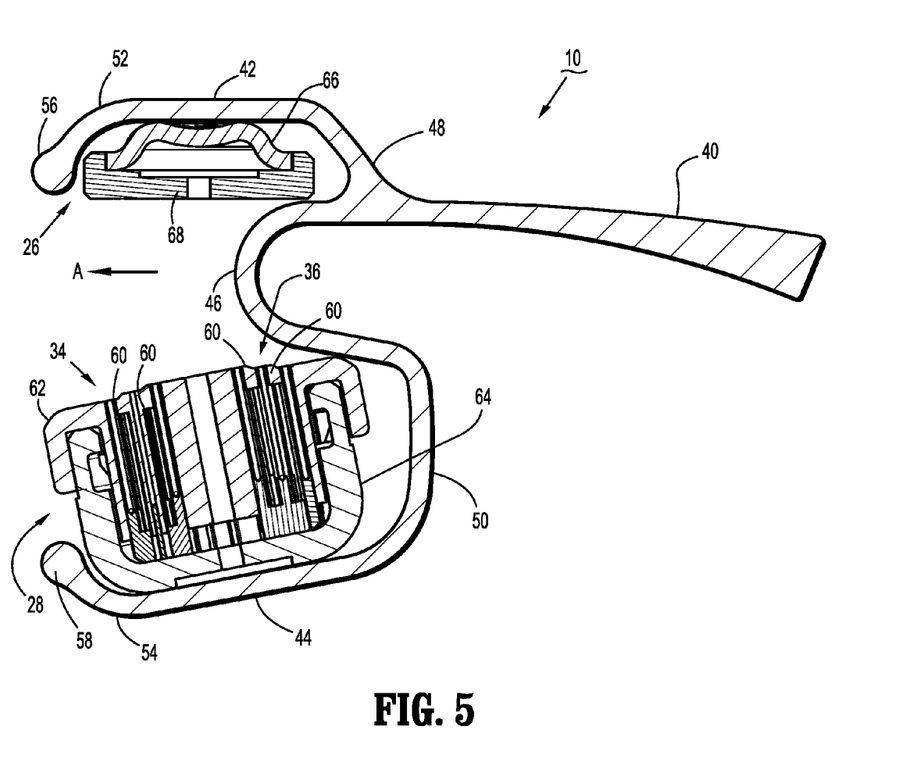
FIG. 5 is a cross-sectional view, taken along line 5-5, of FIG. 2.
Figure 6:
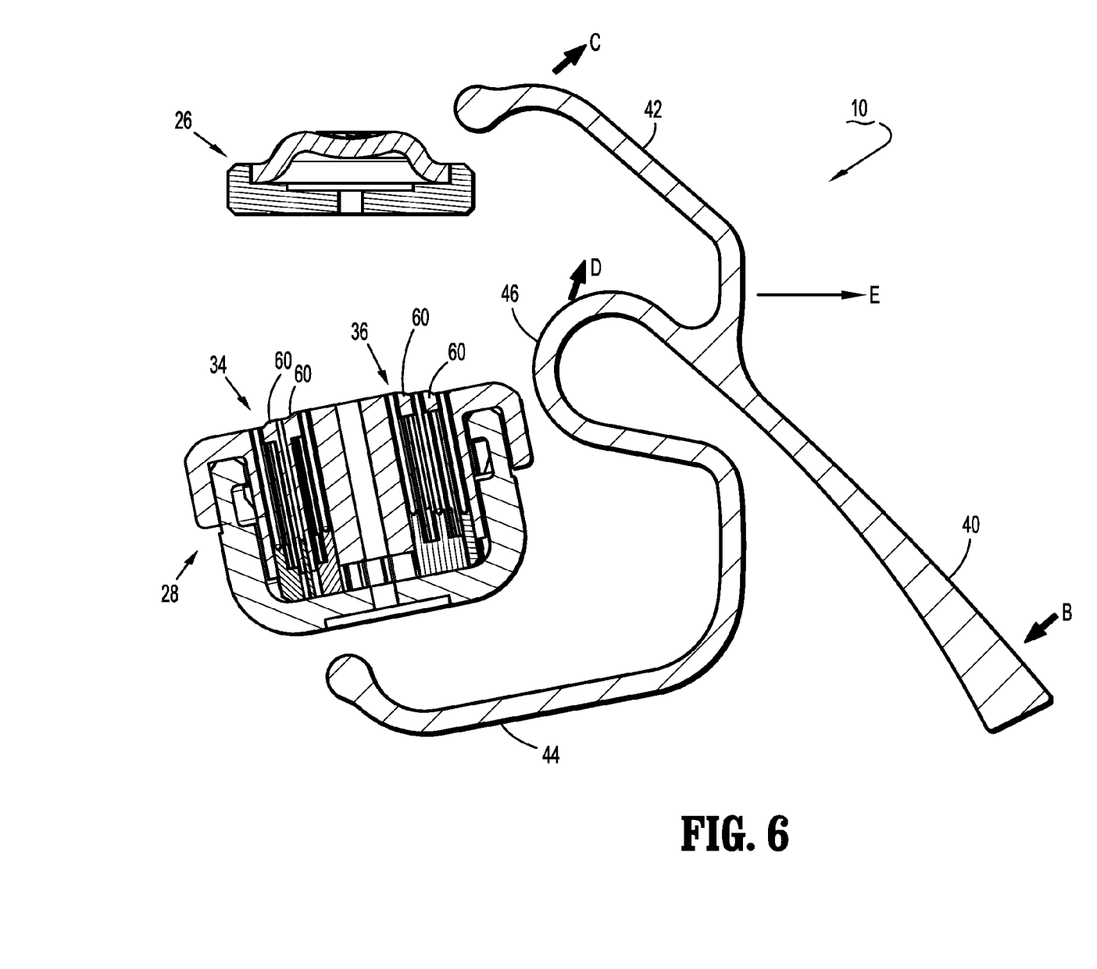
FIG. 6 is a cross-sectional view of the jaw restraint of FIG. 1 being removed from the jaw assembly.

Referring now to FIGS. 5 and 6, and initially with respect to FIG. 5, the use of jaw restraint 10 to stabilize anvil assembly 26 and cartridge assembly 28 during shipment will now be described. As noted herein above, cartridge assembly 28 includes a plurality of staples 60 provided within first and second rows of staple containing pockets 34 and 36. First and second rows of staple containing pockets 34 and 36 are formed in a plastic body portion 62 of cartridge assembly 28. A generally U-shaped channel member 64 is provided to support body portion 62. Anvil assembly 26 includes an upper anvil member 66 and a lower anvil plate 68 which is provided to crimp staples 60.

Prior to shipment, jaw restraint 10 is positioned about anvil assembly 26 and cartridge assembly 28. Specifically, upper arm 42 of jaw restraint 10 engages and secures anvil assembly 26 while lower arm 44 engages and secures cartridge assembly 28. As shown, inwardly facing projection 46 extends between anvil plate 68 of anvil assembly 26 and body portion 62 of cartridge assembly 28 to thereby inhibit any movement of anvil assembly 26 relative to cartridge member 28 during shipping.

Additionally, first and second lips 52 and 54, along with respective enlarged distal ends 56 and 58, provided on upper and lower arms 42 and 44, respectively, assist in preventing anvil assembly 26 and cartridge assembly 28 from sliding sideways in the direction of arrow A out of jaw restraint 10.

Referring now to FIG. 6, in order to remove jaw restraint 10 from anvil assembly 26 and cartridge assembly 28, finger member 40 is moved or squeezed in the direction of arrow B flexing or compressing inwardly facing projection 46 thereby causing upper arm 42 to move or rotate in the direction of arrow C up and away from anvil assembly 26. This causes upper arm 42 to rotate to an open position relative to lower arm 44. Rotation of upper arm 42 to the open position frees anvil assembly 26 from between inwardly facing projection 46 and upper arm 42. Additionally, movement of finger member 40 in the direction of arrow B, flexes the inwardly facing projection and moves inwardly facing projection 46 slightly in the direction of arrow D to free cartridge assembly 28 from between inwardly facing projection 46 and lower arm 44.

Thereafter, jaw restraint 10 may be drawn sideways in the direction of arrow E away from anvil assembly 26 and cartridge assembly 28 thereby freeing anvil assembly 26 and cartridge assembly 28 from jaw restraint 10. It should be noted that, while jaw restraint 10 is illustrated and described as being removed sideways in the direction of arrow E relative to anvil assembly 26 and cartridge assembly 28, jaw restraint 10 may alternatively be slid longitudinally over anvil assembly 26 and cartridge assembly 28 to slide jaw restraint 10 longitudinally off of anvil assembly 26 and cartridge assembly 28.

In this manner, jaw restraint 10 firmly and robustly secures cartridge assembly 28 relative to anvil assembly 26 during shipping thereby preventing any dislodging of staples 60 from rows of staple containing pockets 34 and 36 due to bumping, shaking etc. of anvil assembly 26 and cartridge assembly 28 during shipping.

Figure 7:
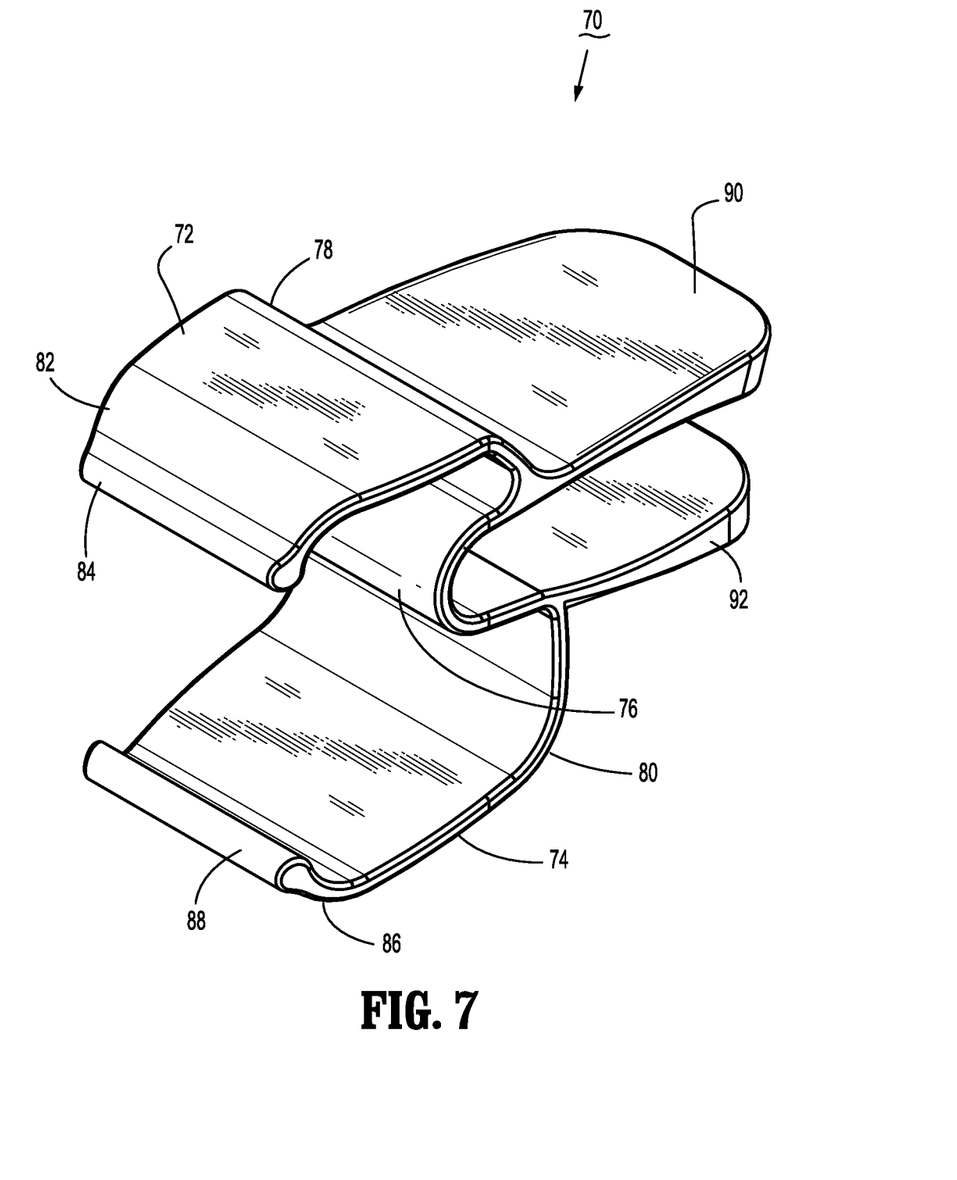
FIG. 7 is a perspective view of an alternate embodiment of a jaw restraint for use with a surgical instrument.
Figure 8:
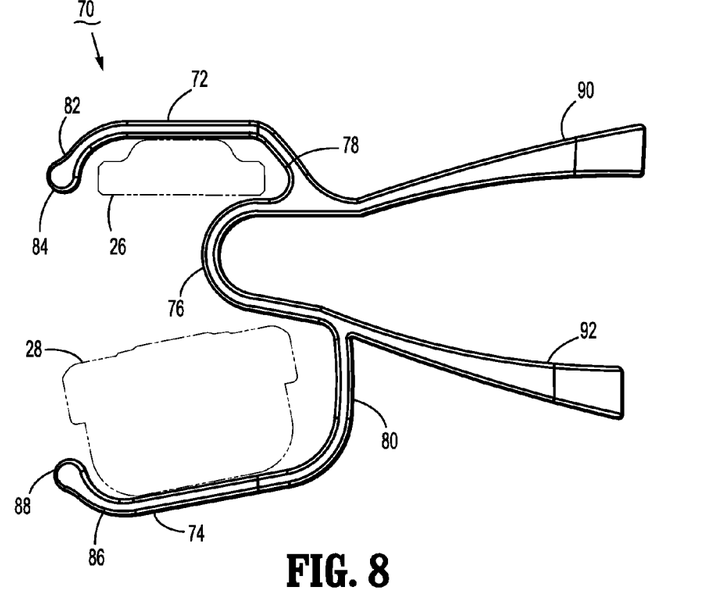
FIG. 8 is a side view of the jaw restraint of FIG. 7 positioned about a jaw assembly.
Figure 9:
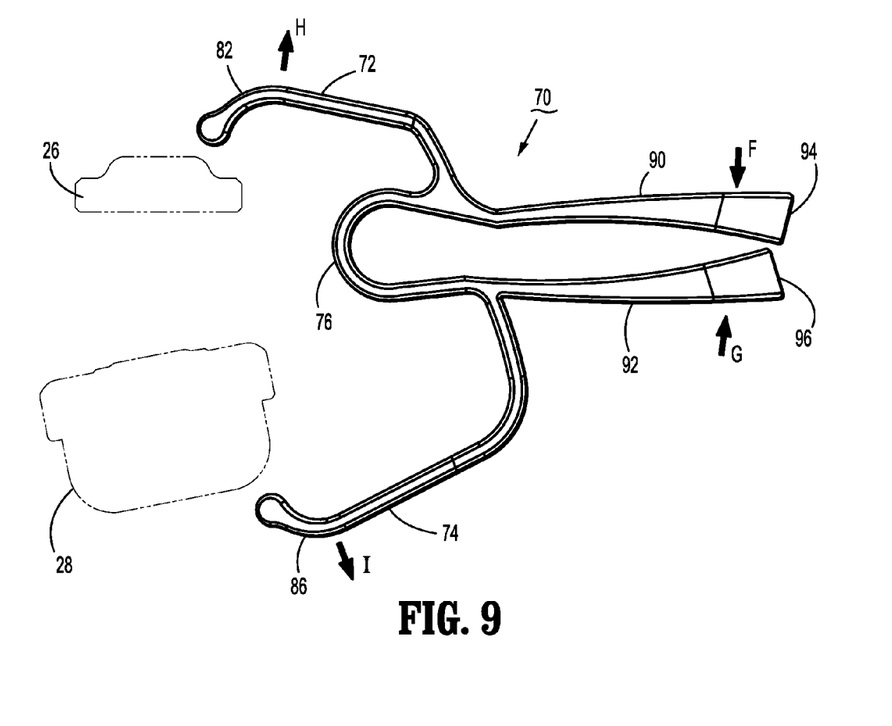
FIG. 9 is a side view of the jaw restraint of FIG. 7 being removed from the jaw assembly.

Referring now to FIGS. 7-9, and initially with regard to FIG. 7, there is disclosed an alternative embodiment of a jaw restraint 70. Jaw restraint 70 is similar to jaw restraint 10 and generally includes a first or upper arm 72 and a second or lower arm 74. An inwardly facing projection 76 is positioned between upper arm 72 and lower arm 74. Upper arm 72 is connected to inwardly facing projection 76 by a first arcuate portion 78 and lower arm 74 is connected to inwardly facing projection 76 by a second arcuate portion 80. In order to prevent sideways movement of a cartridge and anvil assembly such as, for example, cartridge assembly 28 and anvil assembly 26 described herein above, upper arm 72 has an inwardly facing first lip 82 terminating an enlarged distal end 84 and lower arm 74 has an inwardly facing second lip 86 terminating in an enlarged distal end 88.

Jaw restraint 70 differs from jaw restraint 10 described herein above in that jaw restraint 70 includes a first finger member 90 extending proximally from first arcuate portion 78 and a second finger member 92 extending proximally from second arcuate portion 80. The provision of first and second finger members 90 and 92 provide additional leverage to compress inwardly facing projection 76 and thus separate upper arm 72 from lower arm 74.

Referring now to FIGS. 8 and 9, the use of jaw restraint 70 to secure and release anvil assembly 26 and cartridge assembly 28 will now be described. Referring initially to FIG. 8, in the shipping condition, upper arm 72 engages anvil assembly 26 and secures it against inwardly facing projection 76. First lip 82, including enlarged distal end 84, inhibits sideways movement of anvil assembly 26 relative to inwardly facing projection 76. Similarly, lower arm 74 engages cartridge assembly 28 and second lip 86 including an enlarged distal end 88 inhibit sideways movement of cartridge assembly 26 relative to inwardly facing projection 76. As shown, in the shipping condition, first and second finger members 90 and 92 are in a static or spaced apart condition.

Referring now to FIG. 9, in order to release anvil assembly 26 and cartridge assembly 28 from jaw restraint 70, proximal ends 94 and 96 of first and second finger members 90 and 92, respectively, are squeezed together in the directions of arrows F and G. This compresses inwardly facing projection 76 causing upper arm 72 and lower arm 74 to move outwardly in the directions of arrows H and I to the open position. In this open position, anvil assembly 26 and cartridge assembly 28 are free to be removed from jaw restraint 70. Similar to that described herein above with respect to jaw restraint 10, jaw restraint 70 may now be moved sideways relative to anvil assembly 26 and cartridge assembly 28, or may be slid longitudinally along the long axes of anvil assembly 26 and cartridge assembly 28, to release them from jaw restraint 70.

In this manner, jaw restraint 70, incorporating pair of finger members 90 and 92, provides additional leverage for separating upper and lower arms 72 and 74 to release anvil assembly 26 and cartridge assembly 28 from jaw restraint 70.

Figure 10:
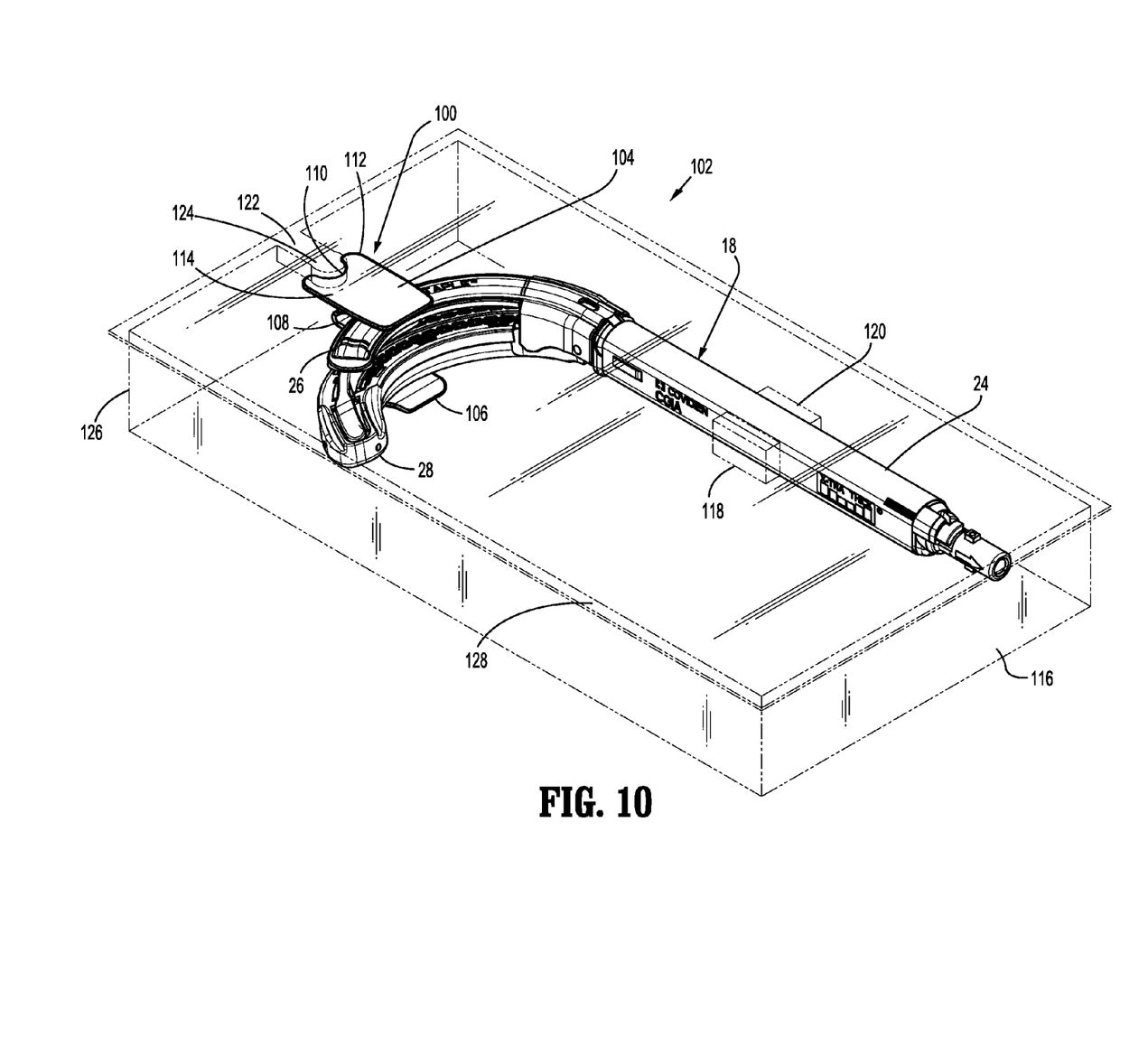
FIG. 10 is a perspective view of an alternate jaw restraint and loading unit of a surgical instrument positioned within a shipping package.
Figure 11:
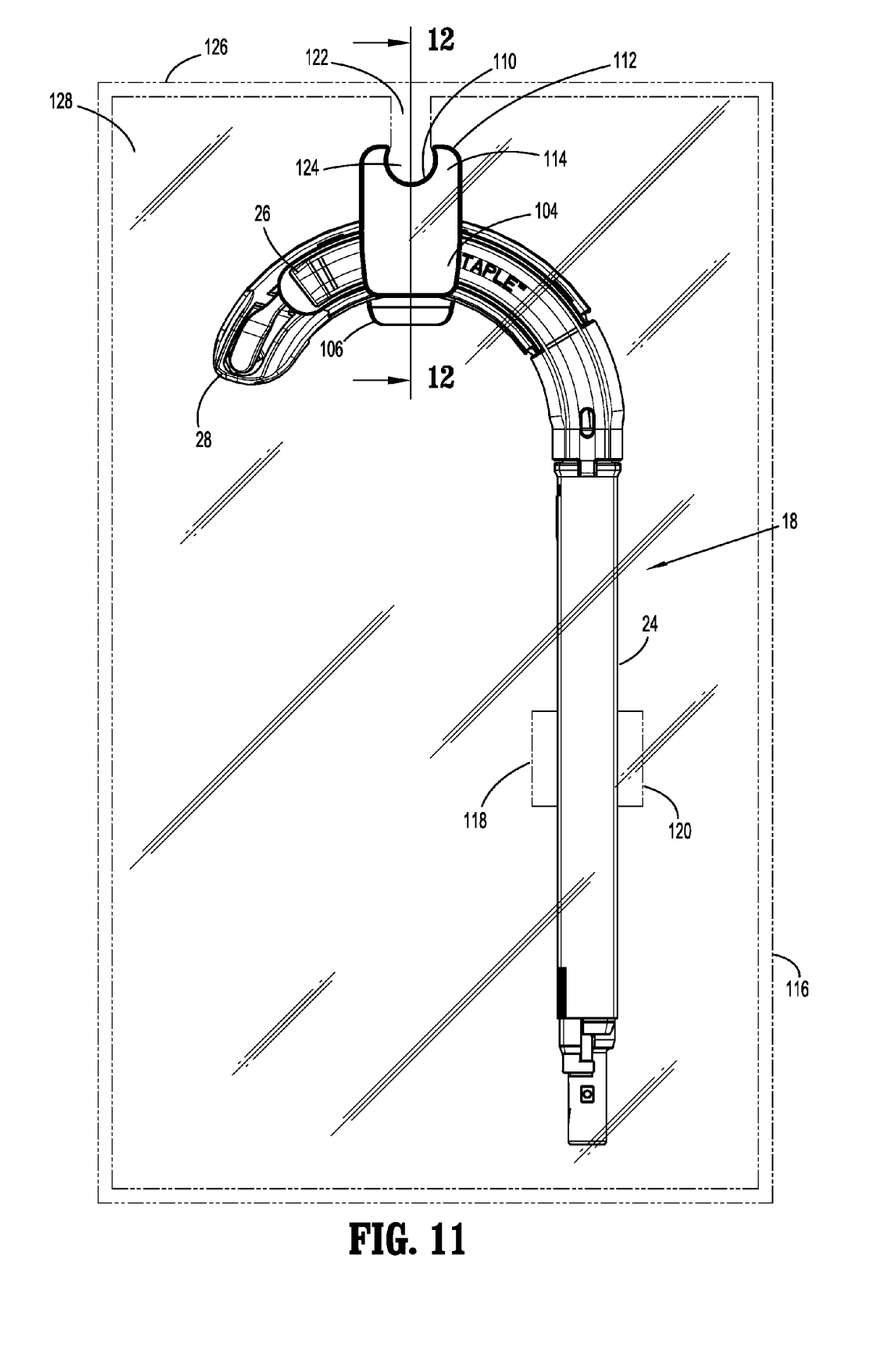
FIG. 11 is a top view of the jaw restraint and loading unit of FIG. 10 positioned within the shipping package.

Referring now to FIGS. 10-15, there is disclosed a further embodiment of a jaw restraint 100 specifically configured for use with a shipping package 102 and loading unit 18 described herein above. Referring initially to FIGS. 10 and 11, jaw restraint 100 generally includes an upper arm 104 and a lower arm 106 separated by an inwardly facing projection 108. In contrast to the finger members described herein above, a cut out 110 is provided in a proximal end 112 of a finger member 114 of jaw restraint 100 to secure jaw restraint 100 to shipping package 102. Shipping package 102 is generally in the form of a box structure 116 having a pair of support blocks 118 and 120 for releasably securing proximal body portion 24 of loading unit 18 within shipping package 102. Box structure 116 includes an inwardly projecting finger 122 having an enlarged end 124. Inwardly projecting finger 122 and enlarged end 124 engage cut out 110 in proximal end 112 of finger 114 to firmly secure jaw restraint 100 to box structure 116. As shown, inwardly projecting finger 122 extends from a sidewall 126 of box structure 116. Box structure 116 can be formed from injection molded plastic or otherwise molded plastic. Blocks 118, 120 can be formed during the molding process. With recesses that engage proximal body portion 24 of the loading unit 18.

Figure 12:
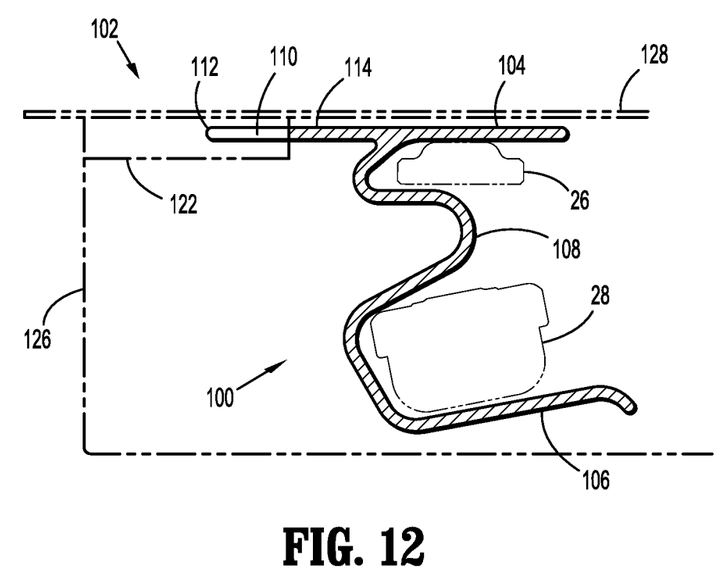
FIG. 12 is a cross-sectional view taken along line 12-12 of FIG. 11.

Shipping package 102 may additionally be provided with a removable cover 128 positioned over box structure 116 to maintain loading unit 18 in a sterile condition (FIG. 12). Cover 128 may be formed from a variety of materials such as, for example, plasticized structures, Tyvek materials, etc.

Figure 13:
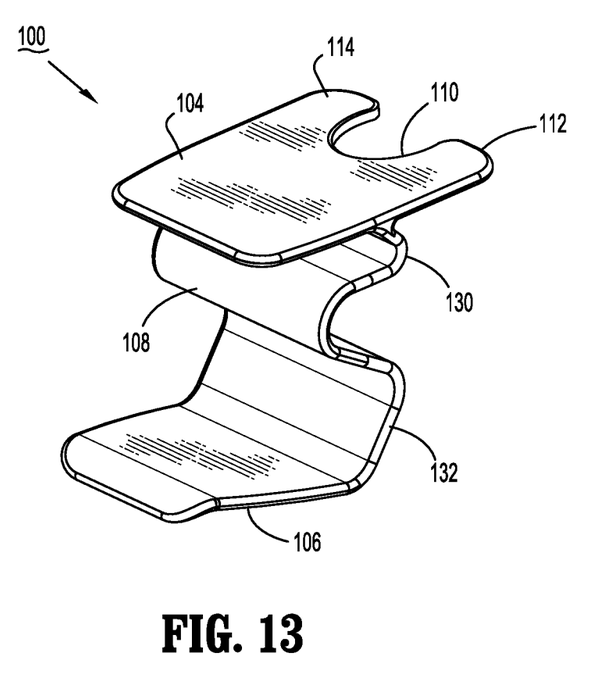
FIG. 13 is a perspective view of the jaw restraint of FIG. 10.

Referring now to FIGS. 12 and 13, jaw restraint 100 further includes a first arcuate portion 130 connecting upper arm 104 to inwardly facing projection 108 and a second arcuate portion 132 connecting lower arm 106 to inwardly facing projection 108. In this embodiment, finger member 114 is formed as a proximal extension of upper arm 104. Alternatively, finger member 114 may be formed as a proximal extension of lower arm 106 or may extend proximally from either first or second arcuate portions 130 or 132, respectively.

Figure 14:
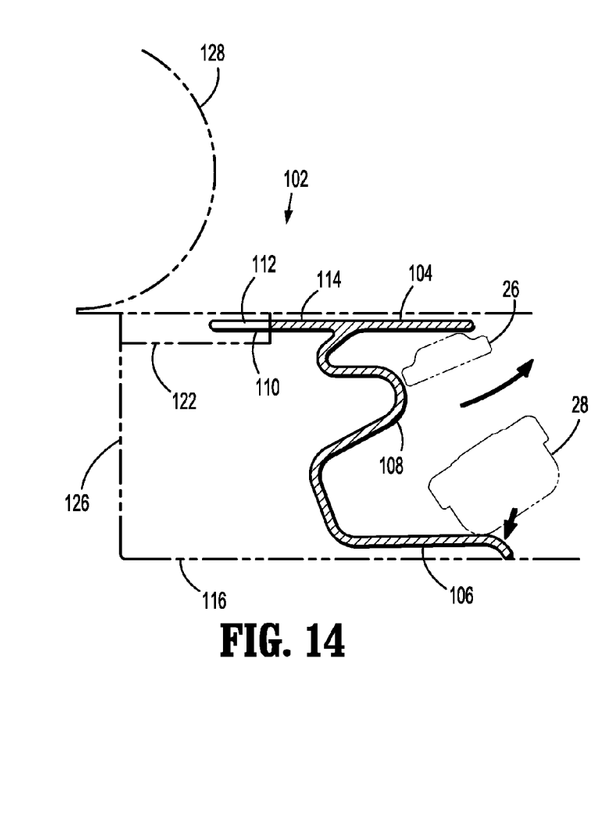
FIG. 14 is a side view, partially shown in section, illustrating the jaws of the loading unit being removed from the jaw restraint of FIG. 10.
Figure 15:
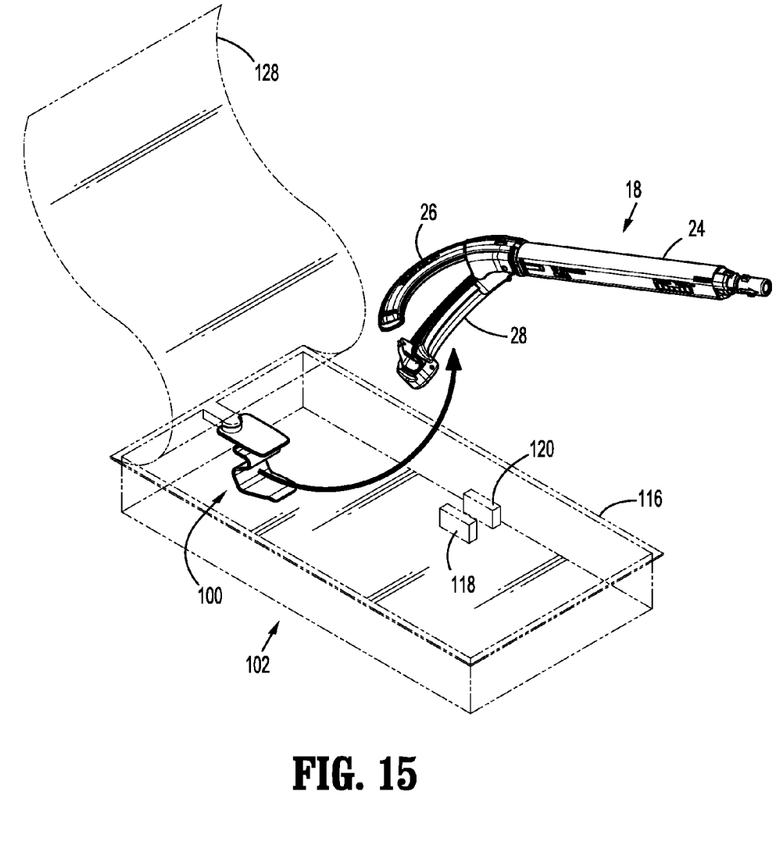
FIG. 15 is a perspective view illustrating the loading unit being removed from the shipping package.

Referring now to FIGS. 10, 14 and 15, and initially with regard to FIG. 10, in use, loading unit 18 is secured within shipping package 102 and jaw restraint 100. Specifically, anvil assembly 26 is secured between upper arm 104 and inwardly facing projection 108 and cartridge assembly 28 is secured between lower arm 106 and inwardly facing projection 108. In this particular embodiment, jaw restraint 100 does not include the inwardly facing lips with enlarged distal ends. In order to maintain anvil assembly 26 and cartridge assembly 28 within jaw restraint 100, proximal body portion 24 of loading unit 18 is releasably secured between blocks 118 and 120 formed in box structure 116. Loading unit 118 is maintained in a sterile condition within shipping package 102 by cover 128.

Referring now to FIGS. 14 and 15, in order to remove loading unit 18 from shipping package 102, cover 128 is initially peeled off box structure 116 to expose loading unit 18. Thereafter, proximal body portion 24 of loading unit 18 is lifted free of blocks 118 and 120 of box structure 116 and anvil assembly 26 and 28 may be pulled free from jaw restraint 100.

Figure 16:
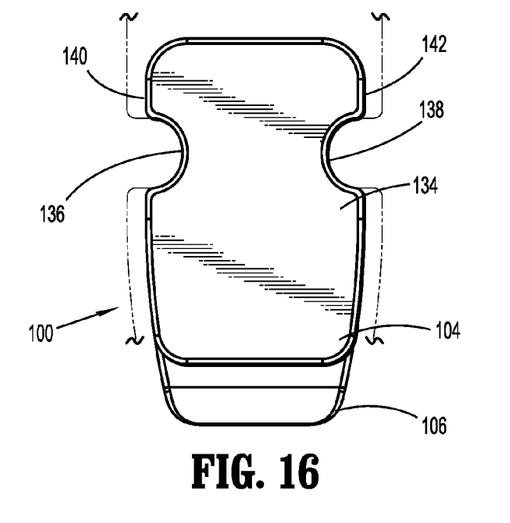
FIG. 16 is a top plan view of an alternate finger member for use in a jaw restraint.

Referring now to FIG. 16 there is disclosed an alternate finger member 134 for use with any of the above described jaw restraints such as, for example, jaw restraint 100. Finger member 134 includes a pair of side cutouts 136 and 138 formed in side edges 140 and 142 of finger member 134. Side cutouts 136 and 138 are provided to cooperate with corresponding structure in a shipping package to secure jaw restraint 100 within the shipping package. More specifically, the box structure includes a pair of fingers with enlarged ends for being releasably disposed in the cut outs 136, 138.

Figure 17:
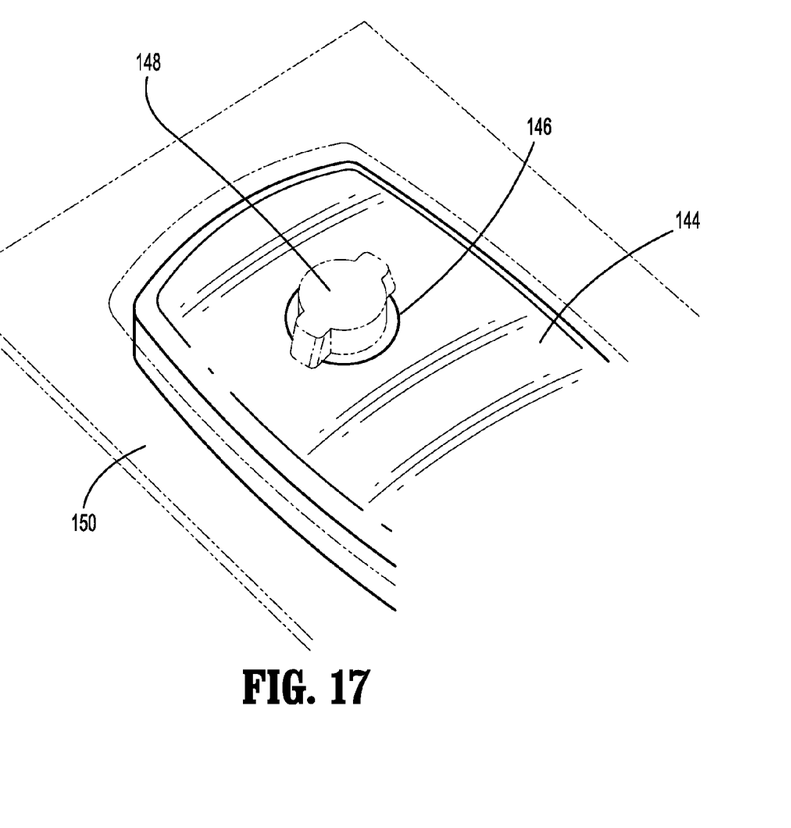
FIG. 17 is a top plan view of a further alternate finger member for use in a jaw restraint.

Referring to FIG. 17, there is disclosed a finger member 144 for use with any of the above described jaw restraints. In this particular embodiment, finger member 144 includes a central cut out 146 formed in finger member 144. Central cut out 146 is provided to receive and engage an upwardly projecting member or plug 148 formed on a shipping package 150 in order to secure the associated jaw restraint within shipping package 150.

It will be understood that various modifications may be made to the embodiments disclosed herein. For example, the disclosed finger members may extend proximally from the upper or lower arms or the first or second arcuate portions. Further, alternative structure may be provided on the underside of the upper and lower arms to secure the cartridge assemblies within the disclosed jaw restraint, such as, for example, adhesives, abraded surfaces, etc. Additionally, the disclosed jaw restraints may be provided with jaw or tool assembly restraining structure on only one of the upper or lower arms. Still further, the assembly retaining structure may be configured to completely encircle the respective anvil or cartridge assembly such that disclosed jaw restraint is slid longitudinally along the respective anvil cartridge assembly to release the anvil cartridge assembly from the disclosed jaw restraint. Therefore, the above description should not be construed as limiting, but merely as exemplifications of particular embodiments. Those skilled in the art will envision other modifications within the scope and spirit of the claims appended hereto.

The invention claimed is:

1. A jaw restraint in combination with a surgical stapler, the jaw restraint comprising:
   a first arm having a first recess to receive a first jaw of the surgical stapler;
   a second arm having a second recess to receive a second jaw of the surgical stapler;
   a projection directed inwardly between the first arm and the second arm;
   a first portion connecting the first arm to the projection; and
   a second portion connecting the second arm to the projection, wherein the first portion is pivotable relative to the second portion about the projection, the first arm is releasably coupled to the first jaw of the surgical stapler, the second arm is releasably coupled to the second jaw of the surgical stapler, and the projection is interposed between the first jaw of the surgical stapler and second jaw of the surgical stapler.

2. The jaw restraint as recited in claim 1, wherein the first and second portions are arcuate, the first portion defining a first opening facing a first direction, the second portion defining a second opening facing the first direction.

3. The jaw restraint as recited in claim 2, wherein the projection is arcuate and has an opening facing a second direction generally opposite the first direction.

4. The jaw restraint as recited in claim 3, further comprising a finger member extending from the first portion.

5. The jaw restraint as recited in claim 4, wherein the finger member extends in a direction opposite to the first direction.

6. The jaw restraint as recited in claim 1, wherein the first arm includes an inwardly directed lip.

7. The jaw restraint as recited in claim 6, wherein the inwardly directed lip includes an enlarged distal end.

8. The jaw restraint as recited in claim 1, wherein the projection is formed from a flexible material.

9. The jaw restraint as recited in claim 8, wherein the projection is formed of a polymeric material.

10. The jaw restraint as recited in claim 1, wherein the first and second arms are pivotable about the projection between a first, jaw retaining position and a second, jaw releasing position.

11. A jaw restraint in combination with a surgical stapler, the jaw restraint comprising:
   a body portion having:
      a first arm having a first recess to receive a first jaw of the surgical stapler;
      a second arm having a second recess to receive a second jaw of the surgical stapler;
      a projection directed inwardly between the first arm and the second arm;
      a first portion connecting the first arm to the projection;
      a second portion connecting the second arm to the projection, the second portion having a greater depth than the first portion, wherein the first arm is releasably coupled to the first jaw of the surgical stapler, the second arm is releasably coupled to the second jaw of the surgical stapler, and the projection is interposed between the first jaw of the surgical stapler and second jaw of the surgical stapler; and a finger member extending from the body portion in a direction opposite of the projection, wherein movement of the finger member urges the first arm to pivot about the projection.

12. The jaw restraint as recited in claim 11, wherein the first and second arms are pivotable about the projection between a first position and a second position.

13. The jaw restraint as recited in claim 11, wherein the first and second jaws of the surgical stapler are retained in the respective first and second arms when the first and second arms are in a first position, and the first and second jaws of the surgical stapler are separated from the first and second arms when the first and second arms are in a second position.

* * * * *